US010188379B2

(12) United States Patent
Lindh, Sr. et al.

(10) Patent No.: US 10,188,379 B2
(45) Date of Patent: Jan. 29, 2019

(54) END EFFECTOR FOR WOUND CLOSURE DEVICE

(71) Applicant: Ethicon, Inc., Somerville, NJ (US)

(72) Inventors: David C. Lindh, Sr., Flemington, NJ (US); Jason Huff, Collingswood, NJ (US); Jesse G. Nawrocki, Annandale, NJ (US); Jason T. Perkins, Easton, PA (US); Robert Scogna, Rocky Hill, NJ (US); Dave Szabo, Branchburg, NJ (US); Tom Beake, Laurence Harbor, NJ (US); Jonathan Wisniewski, Philadelphia, PA (US)

(73) Assignee: Ethicon LLC, Guaynabo, PR (US)

( * ) Notice: Subject to any disclaimer, the term of this patent is extended or adjusted under 35 U.S.C. 154(b) by 375 days.

(21) Appl. No.: 14/844,210

(22) Filed: Sep. 3, 2015

(65) Prior Publication Data

US 2017/0065270 A1    Mar. 9, 2017

(51) Int. Cl.
*A61B 17/04* (2006.01)
*A61B 17/06* (2006.01)
*A61B 17/00* (2006.01)

(52) U.S. Cl.
CPC .... *A61B 17/0401* (2013.01); *A61B 17/06166* (2013.01); *A61B 2017/00004* (2013.01);
(Continued)

(58) Field of Classification Search
CPC .... A61B 2017/0414; A61B 2017/0438; A61B 2017/0446; A61B 2017/0448; A61B 2017/045; A61B 2017/0451; A61B 2017/0453; A61B 2017/0454; A61B 2017/0459; A61B 2017/0461; A61B 2017/0462; A61B 2017/0456; A61B 2017/0458; A61B 17/0401; A61B 2017/0403; A61B 2017/0404; A61B 2017/0406; A61B 2017/0408; A61B 2017/0409; A61B 2017/0411;
(Continued)

(56) References Cited

U.S. PATENT DOCUMENTS 5,156,616 A * 10/1992 Meadows .......... A61B 17/0401
411/395
5,571,139 A * 11/1996 Jenkins, Jr. ........ A61B 17/0401
606/232
(Continued)

FOREIGN PATENT DOCUMENTS

CA    2771656 A1    9/2012
EP    1321103    12/2008
(Continued)

OTHER PUBLICATIONS

International Search Report and Written Opinion dated Mar. 31, 2017 for Application No. PCT/US2016/049457, 21 pgs.

*Primary Examiner* — Jonathan Miles
(74) *Attorney, Agent, or Firm* — Frost Brown Todd LLC

(57) ABSTRACT

A suture device with a composite end effector, the composite end effector including a suture with an unmodified fixation element at a distal end and an overlying attachment piece disposed over the proximal end of the unmodified fixation element. The resulting composite end effector has improved strength and avoids the need for affixation methods such as welding or chemical affixation.

16 Claims, 11 Drawing Sheets

(52) U.S. Cl.
CPC ............ *A61B 2017/00964* (2013.01); *A61B 2017/0417* (2013.01); *A61B 2017/0458* (2013.01); *A61B 2017/0461* (2013.01); *A61B 2017/0464* (2013.01); *A61B 2017/06176* (2013.01)

(58) Field of Classification Search
CPC .... A61B 2017/0412; A61B 2017/0427; A61B 2017/043; A61B 2017/0432; A61B 2017/0433; A61B 2017/0435; A61B 2017/0437; A61B 2017/044; A61B 2017/0441; A61B 2017/0443; A61B 2017/0464

See application file for complete search history.

(56) References Cited

U.S. PATENT DOCUMENTS

| | | | |
|---|---|---|---|
| 6,241,747 | B1 | 6/2001 | Ruff |
| 6,264,675 | B1 | 7/2001 | Brotz |
| 6,306,159 | B1 * | 10/2001 | Schwartz ........... A61B 17/0401 606/148 |
| 6,730,112 | B2 | 5/2004 | Levinson |
| 8,709,183 | B2 | 4/2014 | O'Neill |
| 9,011,487 | B2 | 4/2015 | Lindh, Sr. et al. |
| 9,439,644 | B2 | 9/2016 | Lizardi |
| 9,707,069 | B2 | 7/2017 | Kumar |
| 2001/0008971 | A1 * | 7/2001 | Schwartz ........... A61B 17/0401 606/232 |
| 2001/0021855 | A1 * | 9/2001 | Levinson ........... A61B 17/0057 606/144 |
| 2003/0065361 | A1 * | 4/2003 | Dreyfuss ........... A61B 17/0401 606/232 |
| 2003/0233022 | A1 | 12/2003 | Vidlund et al. |
| 2004/0032332 | A1 * | 2/2004 | Schiebler ............. G09F 3/0311 340/572.9 |
| 2004/0193217 | A1 * | 9/2004 | Lubbers ............ A61B 17/0401 606/232 |
| 2004/0231678 | A1 * | 11/2004 | Fierro .............. A61B 17/06109 128/885 |
| 2005/0004576 | A1 | 1/2005 | Benderev |
| 2005/0049635 | A1 * | 3/2005 | Leiboff ............ A61B 17/0401 606/213 |
| 2005/0222619 | A1 * | 10/2005 | Dreyfuss ............ A61B 17/0401 606/232 |
| 2005/0228415 | A1 * | 10/2005 | Gertner ............ A61B 17/0401 606/153 |
| 2006/0293674 | A1 * | 12/2006 | Li ..................... A61B 17/0401 606/273 |
| 2007/0060922 | A1 * | 3/2007 | Dreyfuss ............ A61B 17/0401 606/326 |
| 2007/0135841 | A1 * | 6/2007 | Dreyfuss ............ A61B 17/0401 606/232 |
| 2007/0257395 | A1 | 11/2007 | Lindh et al. |
| 2008/0103528 | A1 * | 5/2008 | Zirps ................. A61B 17/0401 606/232 |
| 2009/0030453 | A1 * | 1/2009 | Daood .............. A61B 17/0401 606/223 |
| 2009/0248067 | A1 | 10/2009 | Maiorino |
| 2009/0248070 | A1 | 10/2009 | Kosa et al. |
| 2010/0087854 | A1 * | 4/2010 | Stopek .............. A61B 17/0057 606/215 |
| 2010/0146770 | A1 | 6/2010 | Morency et al. |
| 2010/0298871 | A1 | 11/2010 | Ruff et al. |
| 2011/0054523 | A1 | 3/2011 | O'Neill et al. |
| 2012/0078298 | A1 * | 3/2012 | Sklar ................. A61B 17/0401 606/232 |
| 2012/0095506 | A1 * | 4/2012 | Mayer ............... A61B 17/0401 606/232 |
| 2013/0085525 | A1 | 4/2013 | Nawrocki et al. |
| 2013/0211451 | A1 * | 8/2013 | Wales ............... A61B 17/0401 606/232 |
| 2014/0081324 | A1 * | 3/2014 | Sengun ............ A61B 17/0401 606/232 |
| 2014/0081325 | A1 * | 3/2014 | Sengun ............ A61B 17/0401 606/232 |
| 2014/0236229 | A1 | 8/2014 | Longo et al. |
| 2014/0316461 | A1 * | 10/2014 | Sklar ................. A61B 17/0401 606/232 |
| 2015/0032157 | A1 * | 1/2015 | Dooney, Jr. ........ A61B 17/0401 606/232 |
| 2016/0106421 | A1 * | 4/2016 | Eliachar ............ A61B 17/0401 606/228 |

FOREIGN PATENT DOCUMENTS

| | | |
|---|---|---|
| WO | WO 2004/037094 A2 | 5/2004 |
| WO | WO 2006/105008 A1 | 10/2006 |
| WO | WO 2010/051506 A1 | 5/2010 |

\* cited by examiner

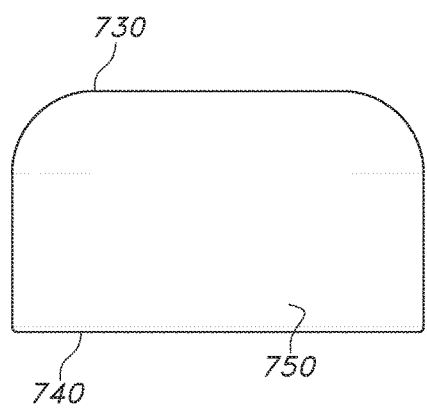
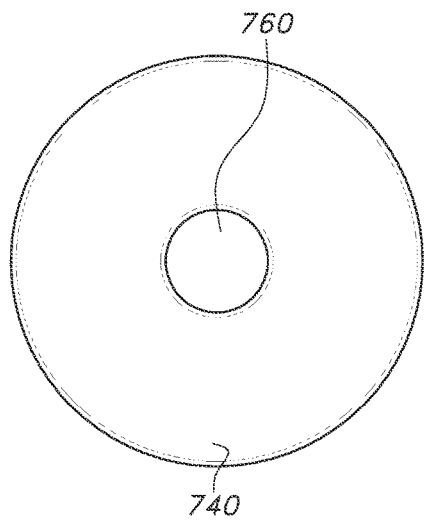
FIG. 13A  FIG. 13B
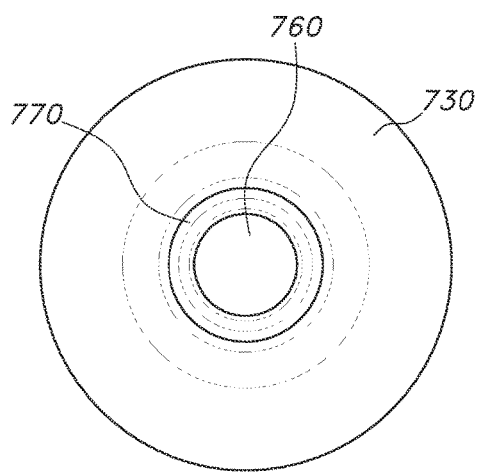
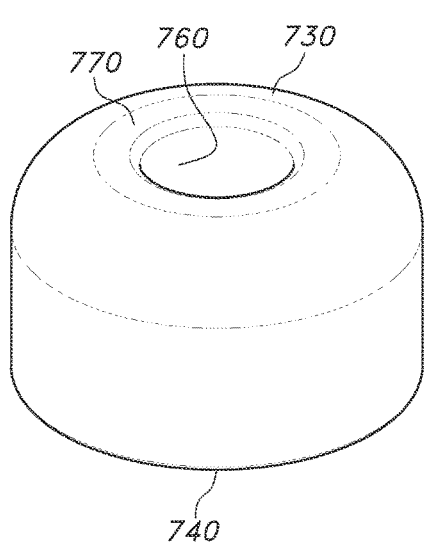
FIG. 13C  FIG. 13D

END EFFECTOR FOR WOUND CLOSURE DEVICE

FIELD OF THE INVENTION

The present invention relates generally to the field of medical devices, and more particularly to self-retaining suture devices having improved composite end effectors.

BACKGROUND

Many wound and surgical incisions are closed using surgical sutures or some other surgical closure device. Self-retaining sutures, also known as barbed sutures, are well known and have gained attention for various medical applications. Typically, self-retaining sutures are constructed with a series of retainers (also known as "barbs" or "protrusions", used interchangeably herein) that extend outwardly from the suture, and function to allow sutures to function without the need for knot tying.

Some sutures, including barbed sutures, have been known to include end effectors at the distal end of the suture to provide a "stop" which prevents or resists the suture from being completely pulled through tissue, while increasing the holding strength of the suture and eliminating the need to tie knots at the distal end to secure the suture. End effectors include, for example, anchors, discs, buttons, knots, tabs, loops, and the like.

Stops may be formed or modified directly from existing suture material by melting or otherwise deforming the distal end of the suture. However, thermally forming operations may undesirably alter the otherwise carefully created physical properties of the suture material immediately adjacent to the stop. For example, welding a tied knot at the end of a suture may potentially alter its crystalline structure and weaken the tensile strength adjacent to the welded structure.

Another known technique to create a stop at the end of a suture is to form the suture from a planar elongated form by removing material lateral to the central longitudinal axis to leave a core suture while leaving material lateral to the central longitudinal axis at the distal end of the suture, such as that described in U.S. Publication No. 2013/0085525. Such stops may be in the form of a tab, also known as a fixation tab. Stops formed in this manner, while eliminating the problem of altering suture properties immediately adjacent to the stop, are planar and may not present sufficient surface area parallel to tissue to adequately anchor the suture's distal end. In some instances, the sides of a stop formed in this manner may break along the length, reducing the ability to serve as an end effector.

Therefore, it would be advantageous to create a stop at the distal end of a suture without affecting the physical properties of the suture immediately adjacent to the stop. Further, there is a need for a stop with increased surface area parallel to tissue prepared in a manner that does not alter the physical properties of the suture material immediately adjacent to the stop. A composite end effector that is formed without welding or altering the molecular structure or physical properties of the suture would be useful.

SUMMARY

The present invention includes a suture device with a composite end effector, increasing strength of an unmodified end effector. The suture device may include an elongated suture body having a proximal end and a distal end; and a composite end effector at the distal end, the composite end effector including: a fixation tab having a length, width and thickness, and an overlying attachment piece, having a tab opening with a length, width and thickness, where at least a proximal end of the fixation tab is inserted into the overlying attachment piece, such that the proximal end of the fixation tab abuts a proximal wall of the overlying attachment piece.

There is also included a method of using a suture as above, including the steps of: inserting a proximal end of the suture device with the composite end effector into tissue; and pulling the suture device through the tissue until a proximal end of the overlying attachment piece abuts the tissue.

There is also included a method of making suture including the steps of: sliding an overlying attachment piece having a tab opening with a length, width and thickness over a suture body having a proximal end and a distal end with a fixation tab at the distal end, the overlying attachment piece being slid in a distal direction along the suture body until the fixation tab is fit into the tab opening.

The present invention may also include a suture device including: an elongated suture body having a proximal end and a distal end, with a knot at the distal end; and a composite end effector at the distal end, the composite end effector including the knot and an overlying attachment piece having an internal opening disposed, where at least a portion of the knot is disposed within the internal opening of the overlying attachment piece. The method may include disposing the overlying attachment piece over the suture body prior to tying the knot, or disposing the overlying attachment piece over the suture body after the knot is tied in the suture body.

BRIEF DESCRIPTION OF THE FIGURES

FIGS. 13A-13D depict alternate embodiments for overlying attachment pieces useful herein.

DETAILED DESCRIPTION

The present invention provides a wound closure device, which may be a self-retaining suture, which has a filamentary body having a proximal end and a distal end and a stop element at the distal end of the filamentary body. The suture may be formed by any suitable method, but preferably is compound profile punched from preformed ribbon or strip of material in a manner described in more detail in U.S. Patent Publication No. 2007/0257395, now U.S. Pat. No. 7,850,894, issued Dec. 14, 2010, which is incorporated herein by reference in its entirety. In some embodiments, the stop element may be generally flat, and may have a rectangular or square-like shape, or in other embodiments it may take a more oval or circular shape. In other embodiments, a stop element may be a tied knot, which avoids the need for pre-forming a stop concurrently while forming the suture.

As used herein, the term "stop element" generally refers to a device at the trailing (or distal) end of the suture, and may also be termed an "anchor", or an "end effector". End effectors include, for example, anchors, discs, buttons, knots, fixation tabs, loops, and the like. One type of end effector that may be useful in the present invention includes a tab designed, similar to that described in U.S. Publication No. 2013/0085525, the entire contents of which are incorporated by reference herein. Another commonly used end effector is a knot, which is tied at a distal end of a suture. While the aforementioned tab design and knot design are useful, the present invention seeks to provide an improved end effector that gives enhanced stopping and holding power while avoiding intolerance and other issues during and after surgical procedures. The discussion below describes an improved end effector. The improved end effector begins with an initial stop, such as a tab or a knot, however, any known existing end effector can be used as the starting point for the improved composite end effector described herein. The resulting combination of an end effector with an overlying attachment piece disposed thereon is termed a "composite end effector".

Figure 1:
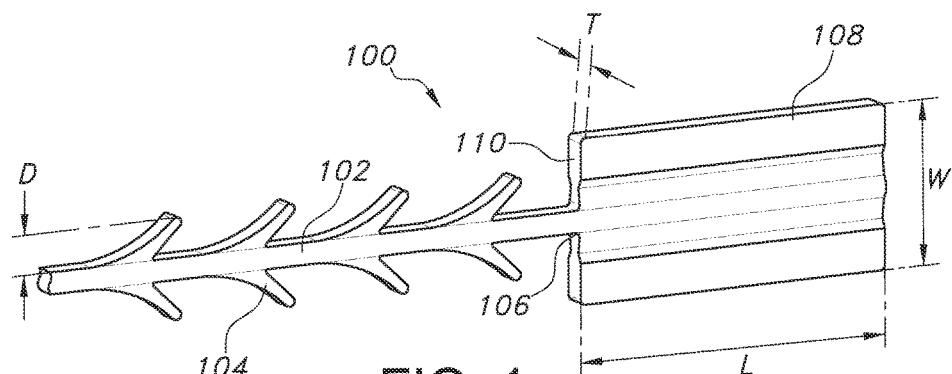
FIG. 1 shows a prior art suture device with a rectangular end effector.

FIG. 1 shows a prior art suture device 100 including an end effector, which is in the form of a fixation tab 108, which is located at a distal end 106 of an elongated suture body 102. The suture body 102 may be any known suture body having any desired cross sectional configuration, such as circular, triangular, or other configuration, and generally has a longitudinal central axis between its distal end 106 and an opposed proximal end (not seen in FIG. 1), where the proximal end is an insertion end and may include a tissue penetrating feature, such as a needle. In use, the proximal end is inserted through tissue, and the suture 100 is pulled through tissue until the distal end 106 abuts tissue. For self-retaining sutures, the body 102 may include a plurality of retainers 104, which may be arranged along the suture body 102 in any configuration, including, for example, symmetric, spiral, or in a random orientation. Retainers 104 may be formed by punching or stamping out the suture 100 from a single ribbon or preform material. Alternatively, retainers 104 may be formed by cutting out from an elongated material, such as with a blade, laser, or other cutting means. In preferred embodiments, the entire suture device 100, including the suture body 102, retainers 104, and fixation tab 108 is formed by punching or stamping or cutting from a single ribbon or preform material, thereby forming a unitary structure of desired size and shape. In addition, by forming the device 100 from one single material, the fixation tab 108 is secured to the suture body 102 without the need for affixation methods, such as welding or adhering with chemical or other physical means.

Figure 3:
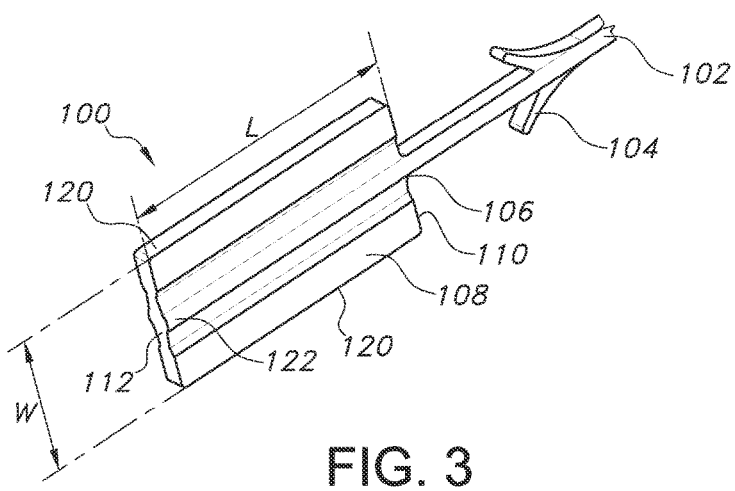
FIG. 3 shows a close-up view of a fixation tab as described in FIG. 1.

FIG. 3 shows a close-up view of the fixation tab 108 of FIG. 1. As can be seen, the fixation tab 108 in this Figure is generally rectangular, having an elongated length (l) and width (w), with leading edge 110 (which is a proximal edge). As used herein, and as seen in the FIG. 3, the length (l) of the end effector is substantially parallel to the central longitudinal axis of the suture body 102. The width (w) of the fixation tab 108 is substantially perpendicular to the central longitudinal axis of the suture body 102. The suture body 102 and the fixation tab 108 may be formed from the same preform or ribbon of material, and therefore are a single unitary construction.

As used herein and throughout this application with reference to each of the components, the term "proximal" shall refer to the end of the suture device that is first inserted into a tissue, while the term "distal" shall refer to the end of the suture device opposite the insertion end. In the suture device of FIG. 1, the distal end generally includes the distal end 106 of the suture body, and also includes the fixation tab 108, while the proximal end (not shown) is the furthest end along the suture body 102 that is opposed from the fixation tab 108, also referred to as the insertion end. End effectors and fixation tabs as described herein also have a proximal end and a distal end. The proximal end 110 of the fixation tab 108 is the edge that is secured to the distal end 106 of the suture body 102. The distal end 112 of the fixation tab 108 is the edge separated from the proximal end 110 by the length (l) of the fixation tab 108. The terms "distal" and "proximal" will generally refer to these directions of the suture device and its various components. Suture devices used herein will be inserted into tissue at the proximal end, and pulled through tissue in the proximal direction.

Figure 2:
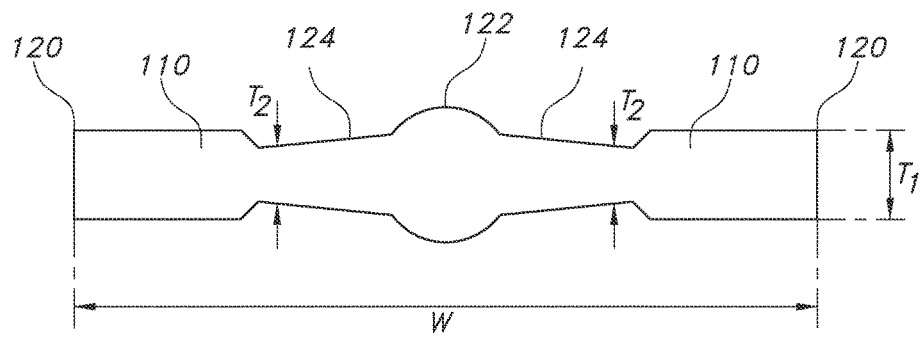
FIG. 2 shows a side view of the end effector of the suture of FIG. 1, as viewed along the central axis.

Known sutures with end effectors such as that in FIGS. 1-3 are typically formed (such as by being stamped, cut or punched) from a single sheet of suture material. Since the single sheet or ribbon of material is used, the thickness configuration of the device 100 is substantially the same throughout the length. That is, the thickness configuration of the end effector 108 is substantially the same as that of the suture body 102. Since the device 100 is stamped from a single piece, the thickness configuration of the fixation tab 108 does not substantially differ from the thickness configuration of the suture body 102. In some embodiments, the elongated central portion of the suture body 102 may have a different thickness than the retainers 104, and this thickness variation may be similar along the length and width of the fixation tab 108. Thus, the fixation tab 108 may have a varying thickness configuration along its width, as may be seen in FIG. 2. Although the description herein describes end effectors in the shape and configuration of rectangular tabs, useful end effectors need not be rectangular, but may be circular, oval, square, or other configurations.

In some embodiments, the thickness (t) of the end effector of FIG. 1 may be approximately 8-25 mils, the width (w)

may be approximately 70-120 mils, and the length (l) may be approximately 39-200 mils. The ratio of the length to the width of a tabbed stop element may be at least 1.5 to about 5.0.

FIG. 2 shows a close up view of the end effector of FIG. 1 as viewed along its length (i.e., so that the width and thickness can be seen). As can be seen, in this embodiment, central region 122 of the end effector extends along the central axis of the suture body 102, and the end effector also includes a first and second outer region 120, first intervening region 124 having thickness $t_2$, and second intervening region 124 also having thickness $t_2$. Thicknesses of each outer region 120 need not be identical, and the thicknesses of the intervening regions 124 also need not be identical. This thickness variation is only one potential configuration, the cross-sectional thickness configuration of the fixation tab 108 may differ from that in the Figures. For example, the thickness may be substantially the same along the entire width of the fixation tab 108.

By way of example, suture devices may be formed from a single sheet (also referred to as a ribbon or preform) of suture-forming material. The ribbon may have a thickness of from about 6-25 mils, typically from 4-12 mils, with a maximum thickness along the central axis of the suture device (i.e., along the central axis of the suture body 102) and/or at first and/or second outer edges, with a minimum thickness at a location between the central axis and the first and/or second outer edges. The length of the ribbon should be at least as long as the desired suture length, including the fixation tab. The width should also be at least as wide as the desired suture width, including the fixation tab.

The holding strength of such fixation tabs may be increased by increasing the dimensions of the fixation tab 108; however, there are practical and clinical limitations on the size and mass that can be used to prevent the suture from further advancing through the tissue. For example, if the device, including tab 108, is too small or thin, it may provide low strength or may fail to restrict movement of the suture device through the tissue. By contrast, if it is too large, it may undesirably leave a large mass within the body of implantation. In addition, larger masses sometimes suffer from difficulties in manufacturing and providing sound structure. Typically, when used clinically, an end effector is implanted into the tissue of the patient and is fully absorbed by the body if it is made from a bioabsorbable or degradable material. If the size and mass of the end effector are too large, there are concerns about tissue reaction and time needed for absorption of the end effector. Further, previous attempts to improve end effectors have relied upon methods such as welding or using chemicals to strengthen the device.

The present invention allows for improved holding strength of an end effector, while avoiding such limitations. In addition, the present invention provides a composite end effector that does not require physically changing or modifying the existing tab that is formed as a part of the initial suture device. The present invention provides a composite device, which includes a starting suture device 100 including an existing end effector (such as tab 108), and an overlying attachment piece disposed over the proximal end 110 of the fixation tab 108. The composite device provides increased surface area at the proximal end 110 of the fixation tab 108, and additionally provides additional holding strength.

The suture device 100 (including suture body 102, retainers 104, and fixation tab 108) may be made of a polymeric, metallic or ceramic material that are absorbable or non-absorbable. In yet another embodiment, the device is made of a polymer material selected from the group consisting of absorbable and non-absorbable homopolymers, random copolymers, block copolymers or blends made from polydioxanone, polyglactin, polyglycolic acid, copolymers of glycolide, lactide, and/or caprolactone, polyoxaesters, poliglecaprone, polypropylene, polyethylene, polyvinylidene fluoride (PVDF), hexafluoropropylene, copolymers of vinylidene fluoride and hexafluoropropylene, polyesters, polyethylene terephthalate, polybutylene terephthalate, glycol-modified polyethylene terephthalate, polytetrafluoroethylene, fluoropolymers, thermoplastic elastomers, ionomers, copolymers of ethylene and methacrylic acid, polyamides, polytetramethylene oxide, polystyrene, polybutadiene, polybutylene, etc. including combinations and/or copolymers of absorbable and non-absorbable materials.

As stated above, the present invention includes two main components: a suture device 100, including an elongated suture body 102 with an end effector 108 at its distal end 106, and an overlying attachment piece to be placed on the proximal end 110 of the end effector 108. The end effector 108 may be a fixation tab, described above, or it may be another stop element (such as a knotted design, shown in FIG. 12). The suture device 100 may be formed by forming the device from a single preform or ribbon of material, thereby ensuring that the suture body 102 and end effector 108 are formed of a unitary construction and include the same materials, whether the end effector is a tab or knotted design. Alternatively, the end effector 108 and suture body 102 may be separate materials that are secured to each other, such as through chemical or physical affixation means.

Figure 4A:
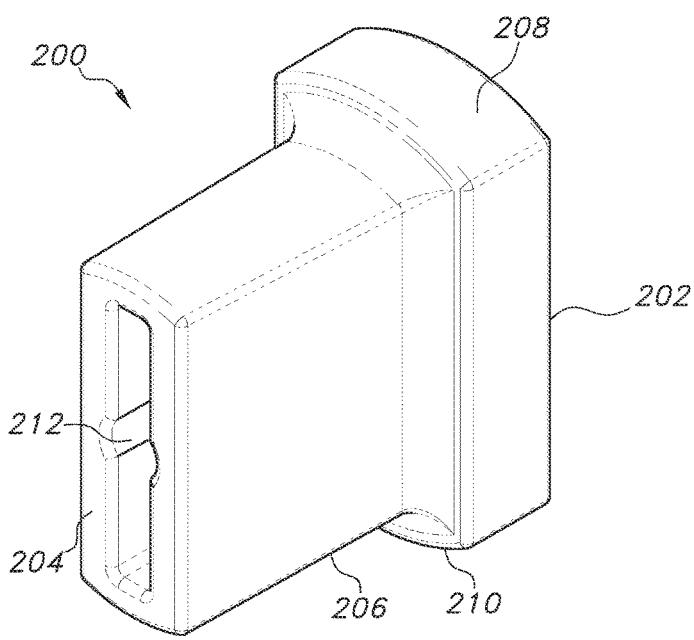
FIG. 4A shows a perspective view of an overlying attachment piece useful in the present invention.
Figure 4B:
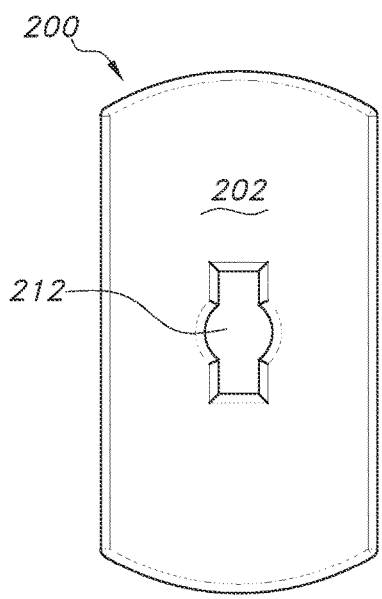
FIG. 4B shows a side view of the overlying attachment piece of FIG. 4A, as seen from the proximal end of the overlying attachment piece.
Figure 4C:
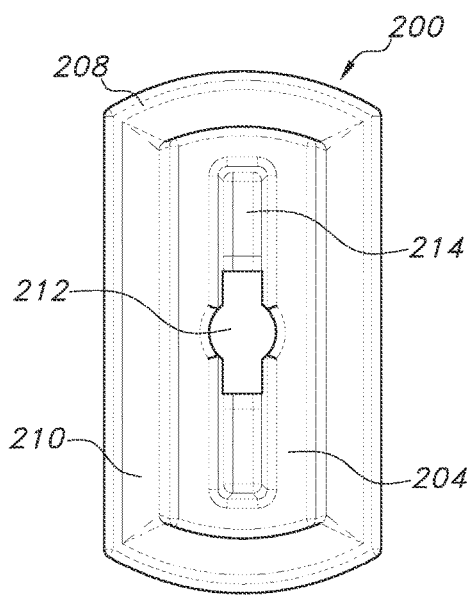
FIG. 4C shows a side view of the overlying attachment piece of FIG. 4A, as seen from the distal end of the overlying attachment piece.
Figure 5:
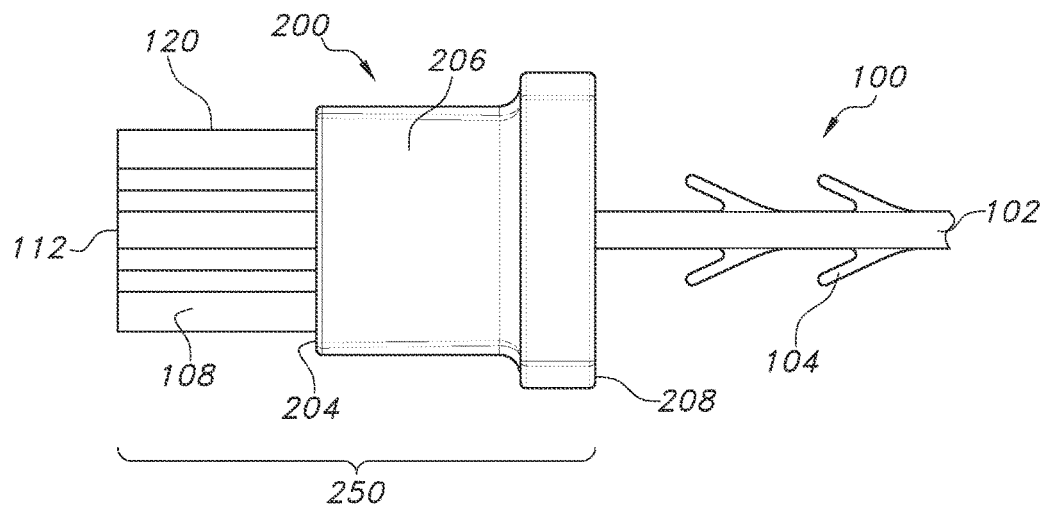
FIG. 5 shows a composite end effector with attachment piece disposed over a fixation tab.

The present invention seeks to take a suture device 100, and modify its end effector 108 in various ways to provide a composite device, with an increased holding strength, while avoiding complications described above. FIGS. 4A-4C show one embodiment of an overlying attachment piece device, which can be used to form the composite end effector. FIG. 5 shows a composite device 250 as formed. The composite device 250 includes a suture having an end effector 108 as described above, with an overlying attachment piece 200 secured to the end effector 108 such that the overlying attachment piece 200 abuts the end effector 108 at its proximal end 110. As noted above, the resulting combination of the overlying attachment piece 200 and end effector 108 is referred to as a composite end effector 250.

In addition to improved holding strength of the device, the composite end effector 250 described herein aids a surgeon during the initial placement of a suture 100 by providing tactile feedback that indicates the proper seating of the composite end effector 250 against tissue. As described above, in use, the user inserts the proximal end of the suture through tissue, and pulls the suture through that tissue until the proximal end of the end effector abuts tissue. With the overlying attachment piece 200 herein, the proximal end of the composite end effector 250 is stronger and more effective. The surface at the proximal end of the overlying attachment piece provides an enlarged and broad surface area over which load can be distributed. In addition, if the overlying attachment piece 200 is snugly fit over the tab 108, the frictional forces exerted on several of the tab's surfaces by the overlying attachment piece, energy and force felt by the tab is distributed to various surfaces of the overlying attachment piece, thereby increasing the strength of the composite end effector. The overlying attachment piece 200 provides statistically significant gains in maximum load, elongation, and energy at break when compared to an unmodified fixation tab (e.g., 108) alone during tensile testing with a metal testing fixture. In addition, it may be useful to include an overlying attachment piece that has a larger front surface with a back extended around the existing tab keeps the piece and its orientation perpendicular to the tissue. The device 200 restrains and orients the tab to utilize whatever material is already there and reinforce the proximal end 110. Device 200 utilizes all available strength and molecular orientation of the suture 100 to maximize performance.

As used herein, the term "energy at break" refers to the tensile energy to break (TEB), which is the total energy absorbed per unit volume of a device up to the point of rupture. In some texts this property has been referred to as toughness. Energy to break is a data output of the tensile test and is a measure of energy absorption by a test device. Here, the composite end effector absorbs energy applied by a user during implantation when it is abutted against tissue. The more effective the composite end effector is at absorbing energy, the more likely it is not only to restrict breaking, but also the more likely it is for the composite end effector to send a tactile signal to the user that it is properly seated. The tensile testing that is performed simulates the mechanical load that the composite end effector might see clinically and measures properties such as maximum load, elongation, and energy at break.

For example, in one suture design with an unmodified tab, as seen in FIG. 1, the tensile strength of such a suture (size 1, PDS suture) is approximately 18 lbs, while the end effector (the tab) may begin to break at 6.5 lbs. The composite end effector (e.g., 250) described herein, which includes the tab and the overlying attachment piece, can double the energy at break as compared to an unmodified tab or end effector, and in some instances, may increase the energy by about 2.5 or about 3.0 times the energy at break of the unmodified tab.

One embodiment of an overlying attachment piece 200 is seen in FIGS. 4A-4C. The overlying attachment piece 200 includes a proximal end 202 and a distal end 204, with a body 206 therebetween. The proximal end 202 may be larger in cross-section than the distal end 204, if desired. At the proximal end 202 of the overlying attachment piece 200 may be an enlarged proximal region 208, identifying the side of the overlying attachment piece 200 at which the proximal end 110 of the fixation tab 108 is to be located. If the enlarged proximal region 208 has a different cross sectional size than the distal end 204 of the overlying attachment piece 200, there may be a taper 210 at which the cross section of the overlying attachment piece 200 changes. As seen in FIG. 4A, for example, the taper 210 serves to smoothly decrease the cross sectional size of the overlying attachment piece 200 from the distal end 204 to the proximal end 202. The use of a taper 210 reduces the cross sectional size of the overlying attachment piece 200, but the piece 200 should still have a sufficient thickness and mass to encapsulate the profile of the existing tab. In this fashion, there remains enough compressive strength to withstand folding/shearing forces exerted by the existing tab on the inner walls of the overlying attachment piece 200. If the existing tab is able to move and flex the wall of the overlying attachment piece 200 significantly, there may be a likelihood of the tab splitting the overlying attachment piece 200, since the wall of the piece 200 may have been too thin or weak. The overlying attachment piece 200 therefore should be small enough to allow for smooth fitting, but have enough mass to avoid or restrict breakage or splitting during use.

The overlying attachment piece 200 includes an opening 212. The opening 212 extends through the central axis of the overlying attachment piece 200, from the distal end 204 to the proximal end 202, as can be seen in FIGS. 4B and 4C. As can best be seen and described in FIGS. 14A-14C below, the opening has a larger dimension at the distal end 204 than at the proximal end 202, and the opening at the proximal end 202 is termed the "suture opening". The opening from the distal end 204 to an internal wall (the abutment wall 214) is the "tab opening". As will be explained below, the fixation tab is inserted into the attachment piece 200 such that at least a portion of the tab is fit into the tab opening.

The opening 212 should extend through the entire attachment piece 200, so that the overlying attachment piece 200 can be placed over the suture body 102 and engage the proximal end 110 of the fixation tab 108. The opening 212 at the proximal end 202 (the "suture opening") should be sized and configured to allow the suture body 102, with retainers 104 if applicable, to pass through the overlying attachment piece 200 without damaging the suture 100 or its components. At the proximal end of the opening 212, there is an internal abutment wall 214, against which the fixation tab 108 is abutted when the composite end effector 250 is prepared. This allows the fixation tab 108 to be inserted at least partially into the opening 212, but the proximal end 110 of the fixation tab 108 abuts the interior of the overlying attachment piece 200 at the abutment wall 214. This restricts the fixation tab 108 from being pulled through the entire attachment piece 200 and holds the tab 108 in place.

The interior of the opening 212, and particularly the opening 212 as defined from the distal end 204 to the abutment wall 214, should be sized and shaped to fit at least a portion of the fixation tab 108, and the opening 212 may have a similar cross section as the thickness configuration of the fixation tab 108. As can be seen in FIGS. 4A-4C, for example, the opening 212 has a larger middle region, which accounts for a larger thickness at the central axis of the suture device 100, including fixation tab 108. Other cross sectional configurations for the opening 212 are contemplated, and should be similar to the width and thickness of the fixation tab 108. Reducing folding and flexion, and keeping the fixation tab 108 oriented perpendicular to the tissue may be useful to resist crack formation and failure, thereby improving the effectiveness of the fixation tab. As will be described below, the length of the opening 212 need not be the same as the length (l) of the fixation tab 108, since the overlying attachment piece 200 need not fully extend along the length (l) of the fixation tab 108. It is desirable that there be enough length within the attachment piece 200 to the rear portion to sufficiently hold the fixation tab 108 therein. Without some length to the slot, the fixation tab 108 would not be restricted enough and may be susceptible to folding. Additionally, if the fixation tab 108 begins to fail while under load, the slot prevents the sides of the fixation tab 108 from moving and/or peeling away from the core. On an unaltered tab 108, once a crack starts and shearing/peeling begins, the sheared material moves out of the way and the tab fails. Here, with the use of a sufficient overlying attachment piece 200, even a sheared tab 108 remains to interfere with and increase the frictional support of all the material behind it.

In some embodiments, the length of the opening 212 may be about half the length (l) of the fixation tab 108, or about three fourths the length (l) of the fixation tab 108. As will be described in more detail, the opening 212, and particularly the tab opening, may have a tapered configuration along its length and/or thickness, creating a snug and tight friction fit of the tab 108 within the piece 200.

Figure 14A:
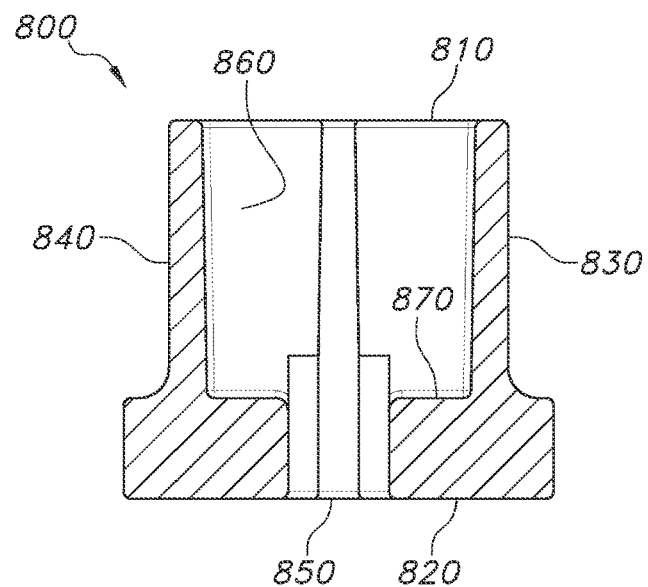
FIGS. 14A-14C show cross-sectional configurations of: (A) an overlying attachment piece; (B) a suture being fed through the overlying attachment piece; and (C) the overlying attachment piece abutted against the fixation tab of the suture.
Figure 14B:
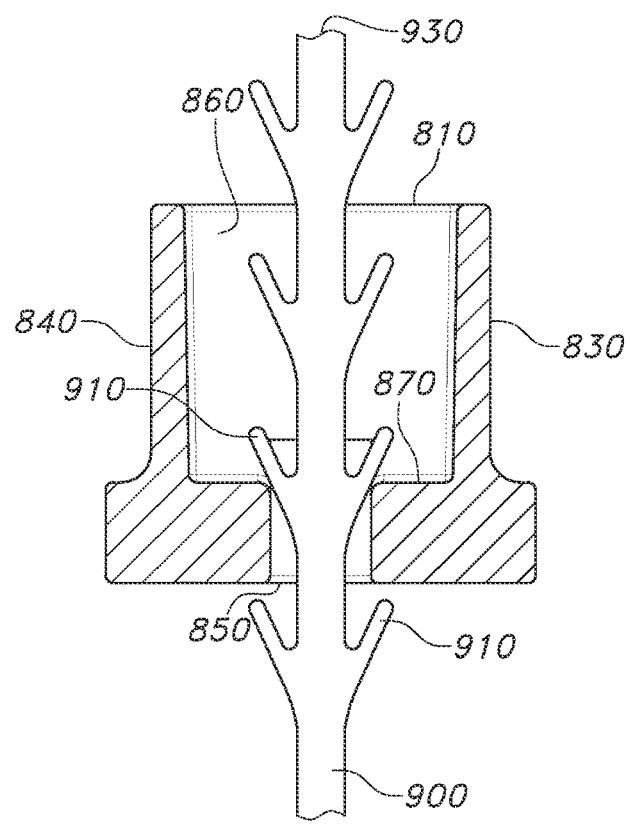
Figure 14C:
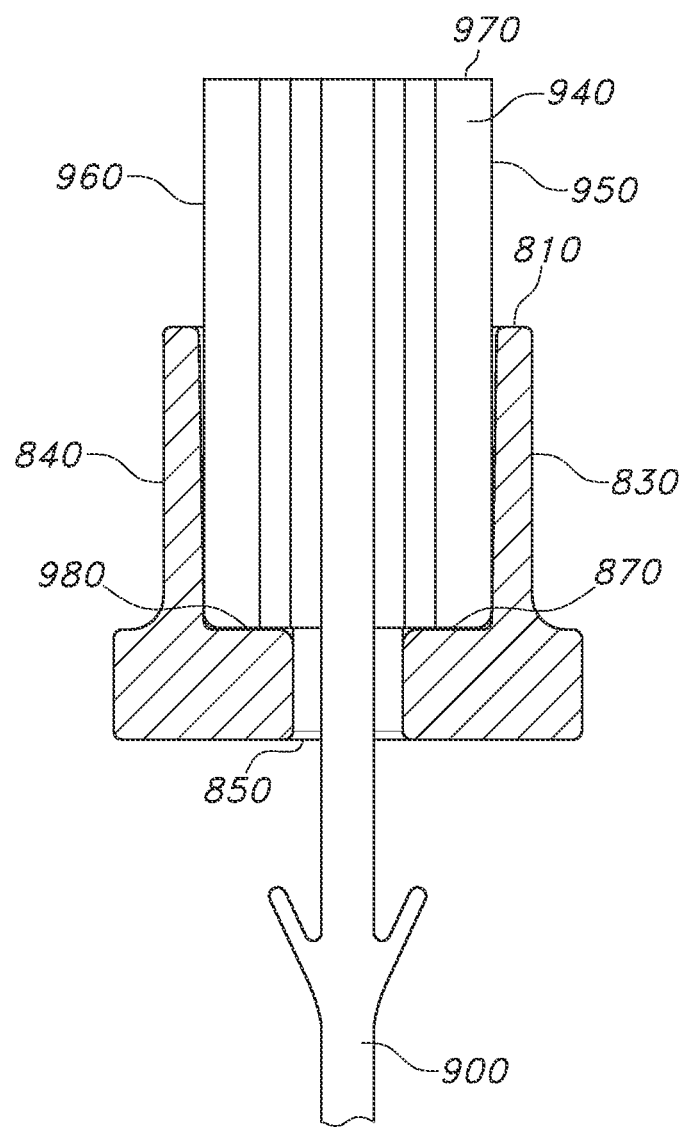

FIGS. 14A-14C depict and demonstrate the attachment of the suture 100 and attachment piece 200, but briefly, the insertion end (the proximal end) of the suture device 100 is threaded through the distal end 204 of the overlying attachment piece 200, and the overlying attachment piece 200 is pulled along the suture length until it reaches the fixation tab 108. The overlying attachment piece 200 is pulled over the fixation tab 108 until the proximal end 110 of the fixation tab 108 abuts the interior abutment wall 214 of the overlying attachment piece 200. At least a portion of the fixation tab 108 is disposed into the opening 212. Since the overlying attachment piece 200 is designed to enhance the proximal end 110 of the fixation tab 108, the overlying attachment piece 200 need not fully cover the fixation tab 108 along its entire length (l). That is, the distal end 112 of the fixation tab 108 may "stick out" through the overlying attachment piece 200, as can be seen in FIG. 5.

As can be seen in FIG. 5, the suture device 100 has been inserted through the opening 212 in the overlying attachment piece 200, and the overlying attachment piece 200 has been moved along the suture body 102 until the fixation tab 108 has been inserted at least partially through the opening 212. The proximal region 208 and the proximal end 202 cover the proximal end 110 of the fixation tab 108, such that the proximal region 208 and proximal end 202 will abut tissue when the suture device 100 is implanted into tissue. Any amount of the fixation tab 108 may extend beyond the distal end 204 of the overlying attachment piece 200 so long as the fixation tab 108 may be held perpendicular to the tissue with its face 110 restrained while under load. By including the overlying attachment piece 200 overlaying the proximal end 110 of the fixation tab 108, there is an increased surface abutting tissue upon implantation. This increased surface improves the strength of the device, and provides a tactile sensation to the user implanting the suture device 100. In addition, given the frictional fit of the tab 108 in the piece 200, there is a greater displacement of energy and force to the attachment piece 200, strengthening the composite end effector 250.

FIGS. 14A-14C show a cross-sectional views of an overlying attachment piece and suture as the suture is being fed through the overlying attachment piece. FIG. 14A shows a cross sectional view of an exemplary overlying attachment piece 800. It is noted that the attachment piece 800 in FIGS. 14A-14C is the same attachment piece as described in FIG. 4 above. The piece 800 includes a distal end 810 and proximal end 820 defining the body, with side walls 830 and 840. At the proximal end 820, there is a suture opening 850, leading to a tab opening 860. The tab opening 860 is larger in size than the suture opening 850. The tab opening 860 is defined by the distal end 810, side wall 830, side wall 840 and tab abutment wall 870. The size of the suture opening 850 should be large enough to allow a suture, including any retainers thereon, to be fed through the attachment piece 800 without damage to the suture or its components, but not so large that the retainers can back out of the attachment piece 800. The length of the tab opening 860 (from distal end 810 to abutment wall 870) may be any length, and should be about 50% to about 100% the length of the tab that is to be inserted into the piece 800. The width of the tab opening 860 (measured from the inside of first wall 830 to inside of second wall 840) should be sufficient to snugly fit the sides of the fixation tab that is to be inserted into the piece 800. The side walls 830, 840 may have a tapered angle, such that the length at the abutment wall 870 may be smaller than the length at the distal end 810. Since the tab is inserted into the piece 800 at the distal end 810 and fed into the piece 800, with a tapered configuration, the tab experiences increasing friction and tightness as it is inserted. There may also be a tapered configuration of the thickness, to create increasing friction and tightness on the surfaces of the tab as it is inserted.

FIG. 14B shows a suture 900, with retainers 910, being fed into the attachment piece 800. The suture has a proximal end (e.g., 920) and a distal end (e.g., 930), with the proximal end 920 being the insertion end and the distal end 930 being the trailing end. The proximal end 920 of the suture 900 is inserted into the distal end 810 of the attachment piece 800, and passes through the entire length of the piece 800. As can be seen, the suture opening 850 is large enough to allow for the suture 900 and its components (such as retainers 910) to be fed through without damage to the suture 900.

FIG. 14C shows the suture 900 as it is completely fed into the attachment piece 800, such that the unmodified end effector (here, a fixation tab 940) is seated into the tab opening 860. As seen, the suture 900 has been pulled through the piece 800 until the fixation tab 940 enters the tab opening 860. The fixation tab has a width defined by side walls 950 and 960, and a length defined by distal end 970 and proximal end 980. The proximal end 980 of the tab 940 is abutted against the tab abutment wall 870.

As described above, it is desired that the attachment piece side walls 830 and 840 have a tapered configuration, such that the width of the tab opening 860 is smaller at the abutment wall 870 than at the distal end 810. This tapered configuration allows for the tab 940 to experience increasing tightness and friction as it is fed into the attachment piece 800. The taper may have an angle of about 0.5 to about 2 degrees as compared to the tab walls 950, 960. It cannot be seen in FIGS. 14A-14C due to the cross-sectional cut, but the thickness of the tab opening 860 may also taper, such that the thickness is smaller at the abutment wall 870 than at the distal end 810.

As seen in FIG. 14C, the length of the tab opening 860 is about half of the length of the tab 940, but the tab opening 860 may have a length that is from about 50% to about 75% the length of the tab 940.

After the overlying attachment piece 800 has been disposed into its final position as seen in FIG. 14C (and also in FIG. 5), the composite device is ready for use. The device may include a means for securing the overlying attachment piece in place without application of energy required, for example, there may be a friction fit or snap fit system to hold the composite end effector together. Alternatively, the overlying attachment piece 800 may be secured in place by means of energy (such as heat, radiation, and the like) or chemical affixation means, such as by use of an adhesive. The composite end effector may be used without further affixation.

With reference to FIGS. 4-5, the present invention provides a suture device 100 with composite end effector 250, including a fixation tab 108 and attachment piece 200 as described above. The invention further includes the method of forming a composite end effector 250, by inserting the proximal end of the suture 100 into the overlying attachment piece 200 opening 212, and sliding the overlying attachment piece 200 distally until at least a portion of the fixation tab 108 is fed into the opening 212 and the proximal end 110 of the fixation tab 108 abuts the interior surface of the proximal end 202 of the overlying attachment piece 200. As will be described in greater detail below, an overlying attachment piece (e.g., 200) may be used with a suture 100 including a different end effector than a fixation tab 108. The opening 212 in the overlying attachment piece 200 may be modified to house any size and shape end effector, including, for example, a button, ball, knot, disc, bar, and loop.

A device of the present invention may be packaged as a final device, that is, a suture having the composite end effector already prepared and in place. Alternatively, the suture and the overlying attachment piece may be separately provided to a clinician. In some embodiments, one suture may be provided with multiple overlying attachment pieces, to allow the user to choose which attachment piece to use, or to use a different piece in the event of improper attachment of the attachment piece to the suture.

The present invention further includes a method of using a suture device with a composite end effector 250. The suture 100 with composite end effector 250 is formed. A user inserts the proximal end of the suture device 100 into and through tissue. The user pulls the proximal end through the tissue until the surface of the tissue abuts the proximal end 202 of the overlying attachment piece 200. At that point, the user stops pulling the suture 100 through that section of tissue. The user may continue to insert the proximal end through other sections of tissue as desired, and the composite end effector 250 remains abutted against the first section of tissue through which the suture device 100 was inserted. With retainers 104 disposed along at least a portion of the suture body 102, there is no need for the user to tie a knot to secure the suture in tissue.

The overlying attachment piece 200 may be manufactured by injection molding or any other desired means to arrive at the desired shape and size. The mold may be shaped as the overlying attachment piece, with a central coring pin to serve as the placeholder for the tab opening. The molten polymer material surrounds the pin during molding and after the polymer solidifies, the pin is removed, which creates the slot. Therefore, the pin should have the same dimensions as the desired slot dimensions when designing the mold and coring pins. The overlying attachment piece 200 may be made from the same material as the suture 100, or it may be made from a different material. The overlying attachment piece 200 may be made from a bioabsorbable material, and in some embodiments, may be made from a material that is absorbed into the body of the patient at a rate that is faster than the suture 100. For example, an injection molded attachment piece 200 made from PDS polymer has been shown to provide statistically significant gains in maximum load, elongation, and energy at break when compared to a fixation tab 108 alone during tensile testing with a metal fixture.

The overlying attachment piece 200 should be made to a size that improves the strength and implantation of the device, but not so great that it causes problems after insertion. The mass of the composite end effector 250 (including attachment piece 200 and fixation tab 108 inserted into the overlying attachment piece 200) may be comparable to a conventional five throw knot tower with a size 1 suture. The mass of the composite end effector 250 therefore does not cause an increase in mass that would cause problems in the tissue into which it is implanted. In addition, by including an opening in the overlying attachment piece 200 that is approximately equal to the size of the fixation tab 108, the overlying attachment piece 200 can effectively limit any undesirable tendency of fixation tab to fold and initiate a crack.

Figure 6:
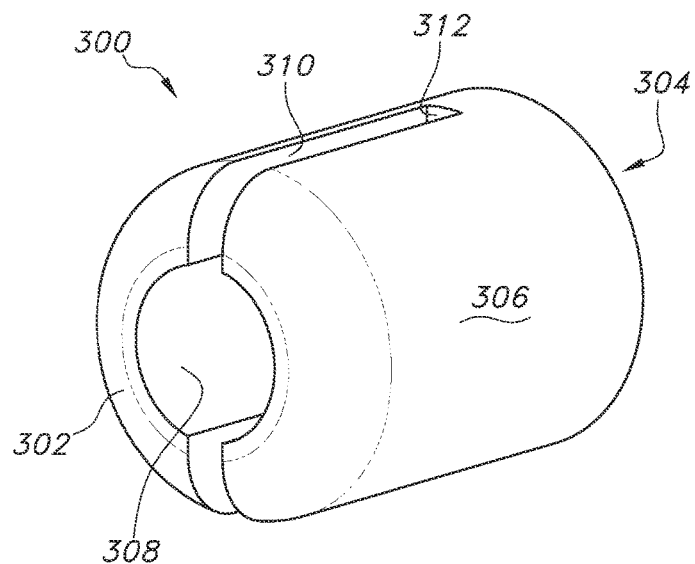
FIG. 6 shows an alternate embodiment of an overlying attachment piece of the present invention.

FIG. 6 depicts an alternate embodiment of an overlying attachment piece useful in the present invention. This Figure depicts a rounded attachment piece 300 having an open slot configuration. As can be seen, the overlying attachment piece 300 includes a distal end 302 and a proximal end 304, with a body 306 therebetween. As described above, the overlying attachment piece 300 includes an opening 308 that spans the entire length of the body 306 from the distal end 302 to the proximal end 304. Having an opening 308 that runs from the proximal end 304 to distal end 302 allows the suture to be fed through the opening 308 to slide the overlying attachment piece 300 distally to the end effector 108.

The embodiment in FIG. 6 shows an open slit design, where the overlying attachment piece 300 includes a slit 310 spanning the entire diameter of the overlying attachment piece 300, commencing at the distal end 302 of the overlying attachment piece 300. As can be seen, the opening 308 is located at or near the axial center of the overlying attachment piece 300, and the slit 310 runs through the center of the opening 308. The slit 310 continues into the body 306 of the overlying attachment piece 300 to a desired length, where it reaches a tab abutment end 312. Notably, the opening 308 still continues through the tab abutment end 312, so that a suture 100 can be fed through the entire length of the overlying attachment piece 300. The tab abutment end 312 is important in this configuration, since the tab abutment end 312 is the area against which the proximal end 110 of the fixation tab 108 abuts during use.

Figure 7A:
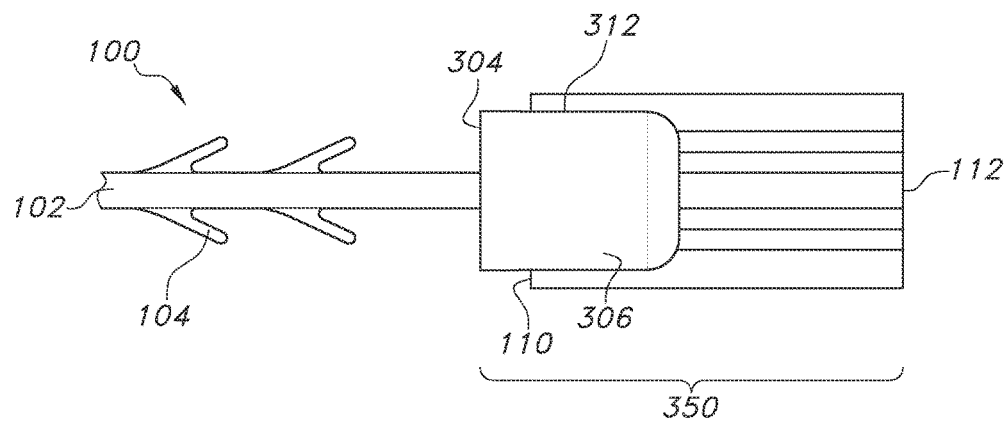
FIG. 7A shows a composite end effector with the overlying attachment piece of FIG. 6 disposed over a fixation tab.
Figure 7B:
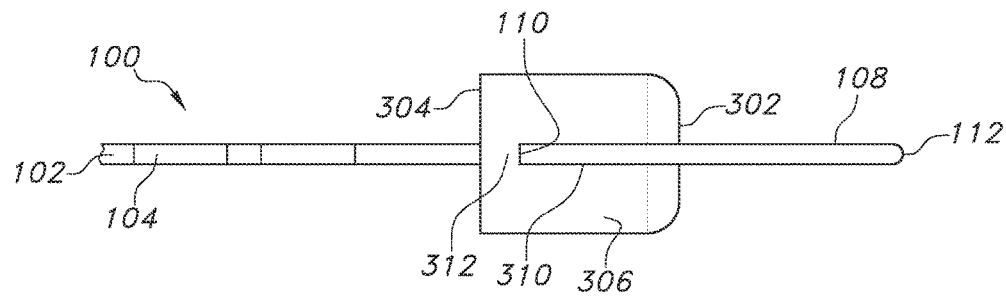
FIG. 7B shows a side view of the composite end effector of FIG. 7A.

FIGS. 7A and 7B show a composite end effector 350 including the fixation tab 108 and open slit attachment piece 300. FIG. 7A shows a top-down view and FIG. 7B shows a side view of the composite end effector 350. As can be seen, the overlying attachment piece 300 is slid distally along the length of the suture body 102, where the distal end 302 of the overlying attachment piece 300 is slid over the fixation tab 108. The suture body 102 is fed through the opening 308. The proximal end 110 of the fixation tab 108 is fed into the slit 310, until the proximal end 110 abuts the tab abutment end 312. The overlying attachment piece 300 may have any length desired, and as seen in these Figures, the length of the overlying attachment piece 300 may be less than the length (l) of the fixation tab 108. If desired, the length of the fixation tab 108 may be approximately equal to or greater than the length of the slit (as measured from distal end 302 to tab abutment end 312). Further, the diameter of the overlying attachment piece 300 need not be equal to or greater than the width (w) of the fixation tab 108. Since the overlying attachment piece 300 of this configuration has an open slit design, the sides of the fixation tab 108 may stick out from the side walls of the overlying attachment piece 300. As with above, the overlying attachment piece 300 may be slid over the suture 100 until the fixation tab 108 abuts the interior of the overlying attachment piece 300 (at the tab abutment end 312), and may be used. If desired, the overlying attachment piece 300 may be secured in place through application of mechanical means (such as friction, snaps, or detents), or application of energy or chemical means, but such affixation is not required.

FIGS. 8 and 9-11 depict alternate embodiments of attachment pieces that may be useful in the present invention. Each of these attachment pieces may be made from the same materials described above, and they may be used in the same way as described above, i.e., by inserting the proximal end of the suture 100 into the opening and sliding the overlying attachment piece distally until the proximal end 110 of the fixation tab 108 abuts an interior section of the overlying attachment piece.

Figure 8:
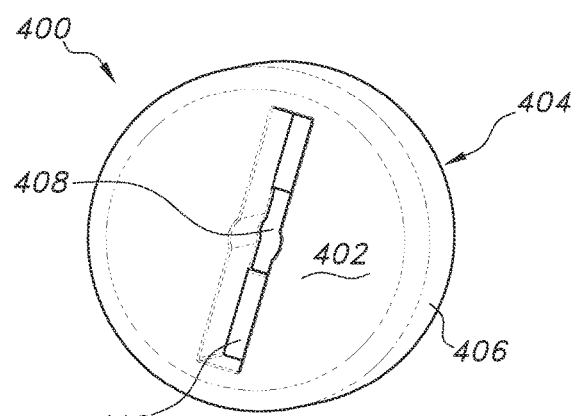
FIG. 8 shows an alternate embodiment of an overlying attachment piece.

FIG. 8 shows a circular attachment piece 400 with a closed slit. This embodiment is similar to the overlying attachment piece of FIG. 4, but is generally cylindrical instead of rectangular. This attachment piece 400 includes a distal end 402, proximal end 404, body 406 therebetween, and an opening 408 extending through the central region of the overlying attachment piece 400 from distal end 402 to proximal end 404. This design includes a closed slit 408, which means there is a slit 408 extending along the diameter of the overlying attachment piece 400, but not extending through the outer circumference of the overlying attachment piece 400. The overlying attachment piece 400 includes a tab abutment end 410 disposed at a location between the proximal end 404 and distal end 402. The slit 408 may be sized and shaped to house a fixation tab 108, and it may be desired that the width of the slit 408 be approximately equal to the width (w) of the fixation tab 108. The length of the slit 408 (measured from distal end 402 to tab abutment end 410) need not be equal or greater than the length (l) of the fixation tab 108, and it may be desired that the length of the slit 408 be less than the length (l) of the fixation tab 108. The surfaces of the overlying attachment piece 400 are desirably smooth or rounded.

Figure 9:
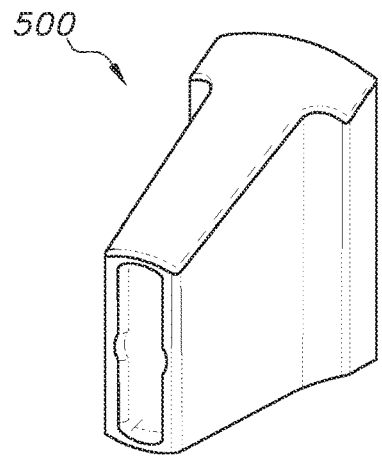
FIG. 9 shows an alternate configuration for an overlying attachment piece.
Figure 10:
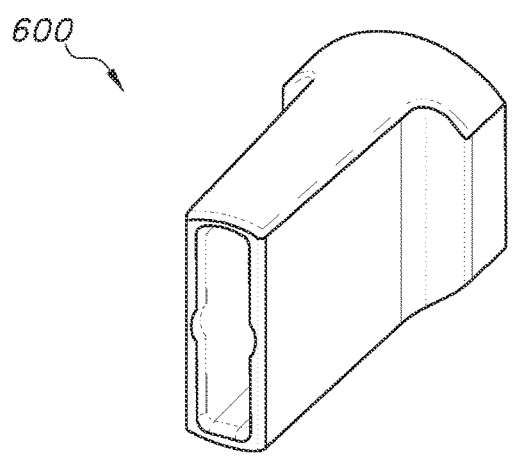
FIG. 10 shows an alternate configuration for an overlying attachment piece.
Figure 11:
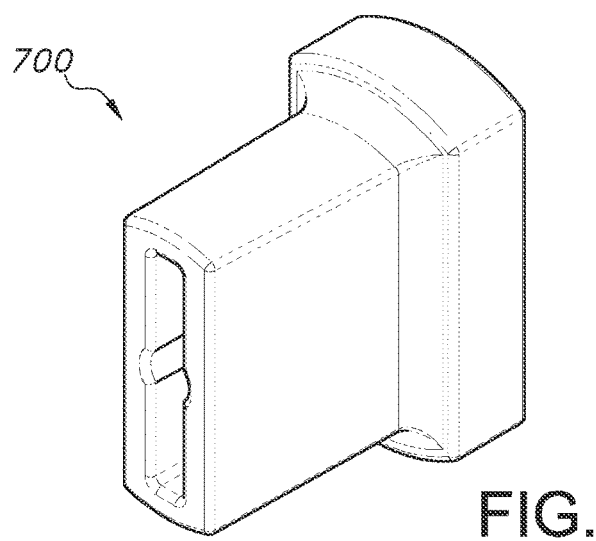
FIG. 11 shows an alternate configuration for an overlying attachment piece.

FIGS. 9-11 depict variations on the embodiment of the overlying attachment piece shown in FIG. 4. In FIG. 9, an overlying attachment piece 500 is shown that includes an externally tapered configuration. In this embodiment, the outer side walls of the body are tapered inward from the proximal end to the distal end. In this embodiment, the proximal region has a larger circumference than the body at the distal end.

In the embodiment shown in FIG. 10, the overlying attachment piece 600 includes a proximal region with a more rounded external configuration. In the embodiment shown in FIG. 11, the proximal region includes top and bottom surfaces that are rounded, while the sides of the proximal region are straight.

Each of these configurations are examples of the modifications that can be made to the overlying attachment piece design and providing useful configurations. The overlying attachment piece may have elongated walls, rounded edges, and/or any other configuration and be useful as described above.

Figure 12A:
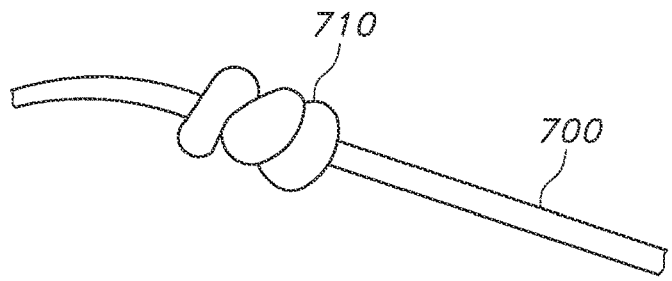
FIGS. 12A-12C show the formation of a composite end effector having an overlying attachment piece disposed over a knotted structure.
Figure 12B:
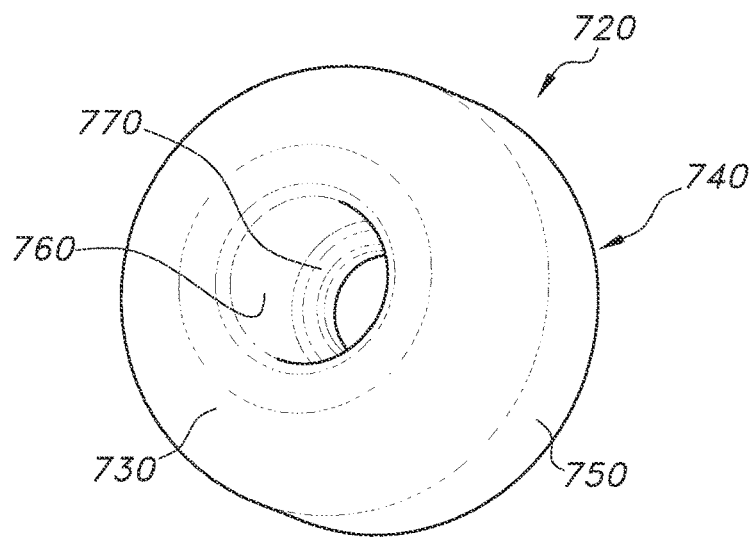
Figure 12C:
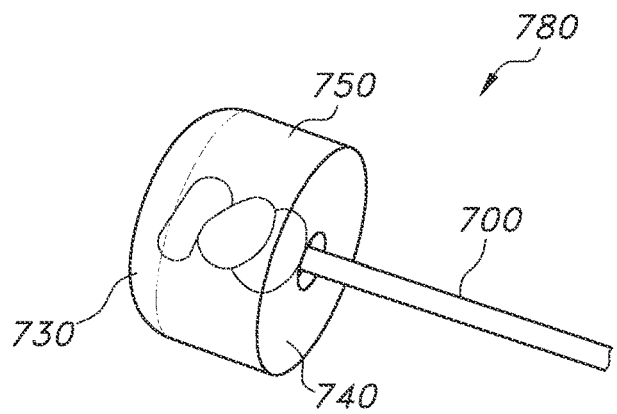

FIGS. 12A-12C show an embodiment of a composite end effector, which incorporates an anchor in the form of a knot with an overlying attachment piece disposed thereon. FIG. 12A shows a conventional suture 700 with a knot 710 tied at a distal end. In this embodiment, the suture 700 may be formed through conventional suture forming means, including extrusion. The knot may be tied with any number of throws, for example, from 1 to 10 throws. The trailing end of the suture 700 located distally of the knot 710 may be trimmed after the knot is formed, thereby making the knot 710 the most distal end of the suture 700. As above, the proximal end of the suture 700 may include an insertion means, such as a needle or other pointed element. The suture 700 may have retainers formed on its surface, including retainers formed by cutting into the surface of the suture 700. FIG. 12B shows an embodiment of an overlying attachment piece 720 useful in securing a suture 700 with knot 710. The overlying attachment piece 720 depicted herein is generally circular in cross section, but other shapes may be used. The overlying attachment piece 720 includes a distal end 730 and a proximal end 740, with a body 750 therebetween, and a central opening 760 extending through the body 750 from distal end 730 to proximal end 740. The diameter of the opening 760 at the distal end 730 is larger than the diameter of the opening 760 at the proximal end 740. This may be achieved, for example, by tapering the size of the opening as it extends from distal end 730 to proximal end 740. Alternatively, the overlying attachment piece 720 may include flange 770 at a location near the proximal end 740 of the overlying attachment piece 720. The flange 770 may be sized so as to restrict the knot 710 from passing through the proximal end 740 of the opening 760. The opening 760 should be large enough in cross sectional diameter to allow the passage of the suture body 700 therethrough without damage.

FIG. 12C depicts the composite end effector 780 formed with a knot 710 and attachment piece 720. The proximal end of the suture 700 is threaded through the distal end 730 of the overlying attachment piece 720, and the overlying attachment piece 720 is slid distally along the suture 700 until at least a portion of the knot 710 is inserted through the distal end 730 of the overlying attachment piece 720. Since the proximal end 740 of the opening 760 has a smaller cross sectional diameter than the distal end 730 of the opening 760, the knot 710 is held abutting the flange 770 and cannot be pulled through the proximal end 740 of the opening 760. Thus, the knot 710 rests within a recessed bore formed by the opening 760 in the overlying attachment piece 720. Once the knot 710 is seated within the opening 760 in the attachment piece 720, the knot 710 experiences a mechanical interference with the inner walls of the opening 760 of the attachment piece 720. This interference fit restricts the knot 710 from sliding out of the opening 760. The distal end of the suture 700 may be threaded through the opening 760 and then a knot 710 may be tied on the distal end, or alternatively, a knot 710 may be formed at the distal end of the suture 700 first, and then the proximal end of the suture may be passed through the proximal end 740 of the attachment piece and moved distally. As noted above, the composite end effector 780 may be secured through application of energy, chemical or other means, if desired. Such additional affixation means are not required.

The overlying attachment piece 720 in FIGS. 12A-12C may be made from a large size extruded suture that is axially drilled, counter bored, optionally countersunk, and cut to an appropriate length. Alternatively, the overlying attachment piece 720 may be formed by injection molding or other process. Forming the attachment piece from an extruded material is helpful when the composite end effector 780 is made from a biodegradable material or a material that is difficult or impossible to mold. Extrusion of the overlying attachment piece 720 may be preferred, as extrusion provides a device with a relatively high degree of molecular orientation, giving different properties in the longitudinal vs transverse direction, which then can increase breaking strength retention. Injection molded parts have fairly uniform properties, although some molecular orientation can occur during a molding process. In some instances, the attachment piece 720 may be formed by extruding a larger size strand (e.g., a strand having a larger outer diameter than the suture 700 to be used) of suture material, which may be the same as the material used for the suture 700 or may be different, and cutting discrete pieces from this extruded strand. For example, the larger size extruded strand may have a circular cross-section, and may be cut into individual disc-like attachment pieces by slicing through the extruded strand at a plane perpendicular to the central axis of the extruded strand. A central hole may be cut into or through the central axis of the resulting disc-like attachment piece, and desirably, there is a countersunk hole cut into the central axis of the disc. It is desirable that the disc-like attachment piece have an outer diameter that is sufficiently large to allow a countersunk hole to be cut into and through the central axis of the attachment piece, where the countersunk hole is large enough to fit and frictionally hold a knot 710.

FIGS. 13A-13D show various views of one embodiment of an overlying attachment piece 720 useful in the embodiment of FIG. 12. The overlying attachment piece 720 includes a distal end 730, proximal end 740, body 750 therebetween, and a central opening 760 extending from the distal end 730 to the proximal end 740. As can be seen, the cross sectional diameter of the opening 760 is larger at the distal end 730 than at the proximal end 740. This may be achieved through the use of a flange 770, as can be seen in the Figures. Alternatively, the opening 760 may be formed by cutting into a body 750 with a tapered cut. The distal end 730 of the overlying attachment piece 720 may have a smooth or rounded edge, which provides a less traumatic experience when the suture is implanted into tissue, as the distal end 730 of the overlying attachment piece 720 is exposed to external tissue after implantation.

Other methods of securing an overlying attachment piece to an existing tab are contemplated herein, for example, an attachment piece may include a hinged side and a snap-fit opposing side, whereby the attachment piece can be opened and snapped into place over the tab.

EXAMPLES

As explained above, the size of the attachment piece's tab opening along its length, width and thickness, as well as the configuration of the opening, may be modified to optimize the mechanical properties provided by the composite end effector. As noted above, the tab opening may be shaped and size to fit the fixation tab (or other end effector if a different end effector is used). As the dimensions of the opening more closely match those of the fixation tab, increasing gains are achieved in load, elongation, and energy at break. To demonstrate the effectiveness of closely matching the configuration of the fixation tab, four different PDS attachment pieces were formed, each with different sizes of tab openings. The overlying attachment pieces were each disposed over a suture, where each suture had a substantially identical fixation tab as that described in FIG. 1. The fixation tab used in this Example had a length of 200 mils, a width of 98 mils, and a thickness of 8 mils just outside the central axis and 12 mils at the sides. The suture diameter was that of a size 1 suture.

The four attachment pieces were labeled Rev-2, Rev-2B, Rev-2C, and Rev-2D. The exterior dimensions of each of the attachment pieces was constant. For each piece, the slot was made incrementally smaller to create a tighter friction fit around the fixation tab upon insertion. Each piece was injection molded using a molding pin to create the tab opening. The molding pin height correlated to the resulting thickness of the tab opening at the central region, while the molding pin wing height correlated to the resulting thickness of the tab opening at the side walls. The purpose of this test was to demonstrate the effect when a more snug and tight fit of the tab in the attachment piece is used.

Rev-2 was an attachment piece that had a core diameter at the central region (along the central axis) of 25 mils from distal end all the way through the proximal end, but had a thickness at the side walls from 18 mils at the distal end to 15 mils at the abutment wall.

Rev-2B was an attachment piece that had a core diameter at the central region (along the central axis) of 22 mils from distal end all the way through the proximal end, but had a thickness at the side walls from 16 mils at the distal end to 13 mils at the abutment wall.

Rev-2C was an attachment piece that had a core diameter at the central region (along the central axis) of 20 mils from distal end all the way through the proximal end, but had a thickness at the side walls from 15 mils at the distal end to 12 mils at the abutment wall.

Rev-2C was an attachment piece that had a core diameter at the central region (along the central axis) of 19 mils from distal end all the way through the proximal end, but had a thickness at the side walls from 14 mils at the distal end to 11 mils at the abutment wall.

The width of the openings at the distal end of each of the pieces was 108 mils and the width of each piece at the abutment wall was 105 mils.

One suture was inserted into each of the attachment pieces, in the manner described with respect to FIGS. 14A-14C.

Tensile testing for each suture was conducted in a custom metal fixture via a benchtop Instron test, with a custom metal test fixture sized and shaped for the suture and/or the composite end effector. This test is more commonly referred to as a shear strength test, and for this example, it is considered a fixation tab shear strength test, since it measures the shear strength of the fixation tab(s) tested. The shear strength of each fixation tab was tested by loading each individual suture into the custom metal test fixture. Each test specimen was introduced into the slit in the fixture top plate such that the fixation tab was immediately in contact with the underside of the plate and the free end of the suture was available on the topside of the plate.

The free end of the suture was gripped with the upper Instron grippers under light tension (enough to keep the suture taut) at a gauge length of 1 inch. The suture was aligned in the center of the grip such that it was perpendicular to the fixture and not angled. Each specimen was pulled at 12 in./min. to the point of fixation tab failure.

Figure 15:
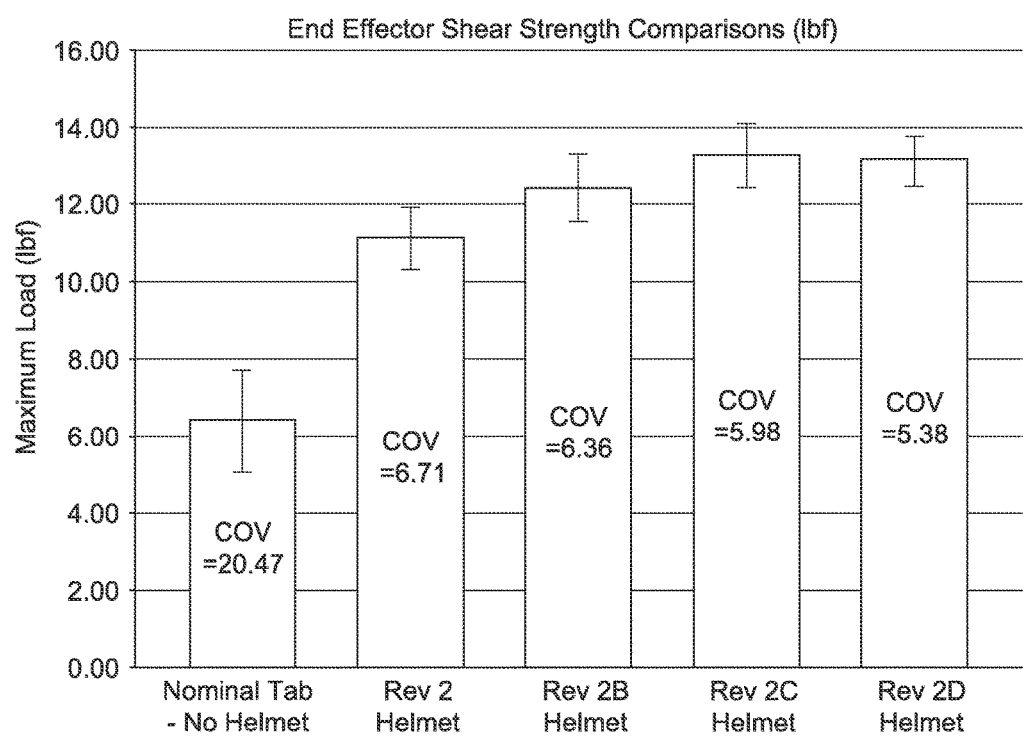
FIG. 15 shows a bar graph of the shear strength values of various products described herein.
Figure 16:
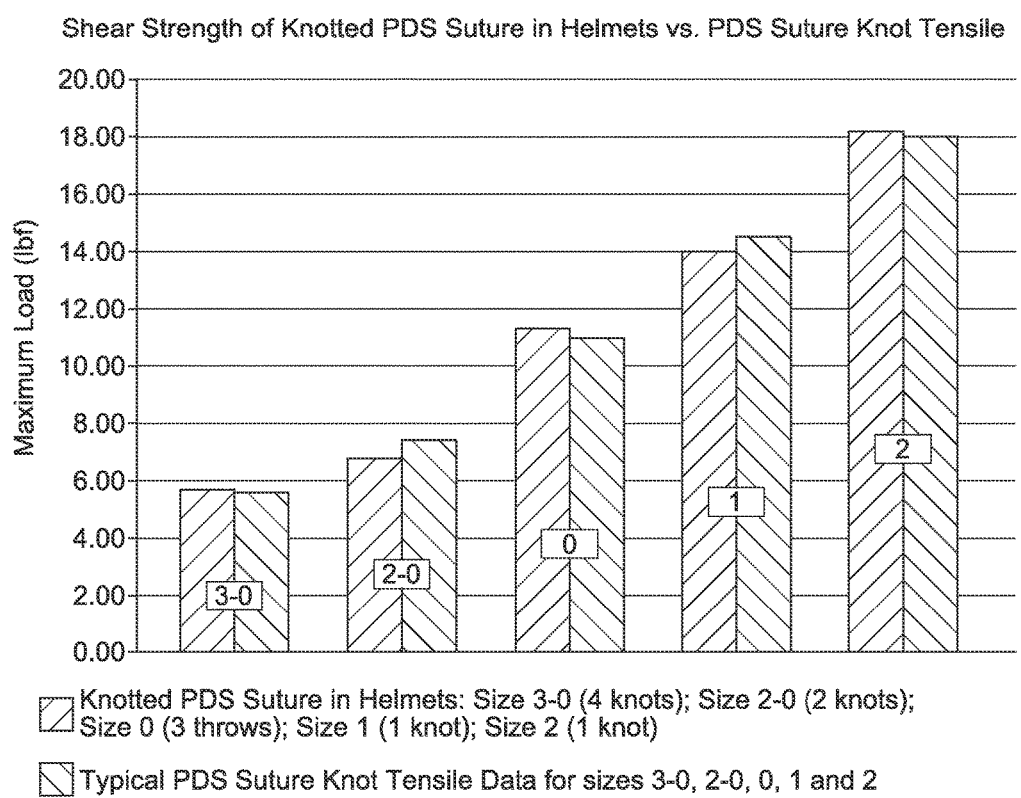
FIG. 16 shows a bar graph of the shear strength values of various products described herein.

Testing was completed on samples of fixation tabs without an overlying attachment piece and the composite sutures with attachment pieces Rev-2, Rev-2B, Rev-2C, and Rev-2D. As noted above, each of the attachment pieces had differing widths and heights, each created a progressively tighter fit of the overlying attachment piece around the fixation tab. It was found that, keeping the external dimensions of the overlying attachment piece constant, and gradually tightening the internal opening dimensions to create a tighter friction fit around the fixation tab, the mechanical performance of the composite end effector improved, i.e. increased end effector shear strength. FIG. 15 shows bar graphs of the resulting shear strength values. Note that the COV (Coefficient Of Variation) is reduced considerably when comparing a fixation tab without an overlying attachment piece to any of the fixation tab plus attachment piece composite end effectors. The percent gains in maximum load, elongation, and energy at break are relative to a suture having a fixation tab with no attachment piece secured thereto. The results are set forth in Table 1 below:

TABLE 1

% Gains in Load, Elongation, and Energy at Break with Various Slot Dimensions in the overlying attachment piece Relative to Fixation Tab alone

|  | Load (%) | Elongation (%) | Energy at Break (%) |
| --- | --- | --- | --- |
| Rev 2 | 73.4 | 34.4 | 129.0 |
| Rev-2B | 93.5 | 49.7 | 188.7 |
| Rev-2C | 107.0 | 51.5 | 205.9 |
| Rev-2D | 105.4 | 50.1 | 201.0 |

As can be seen, Rev-2C and Rev-2D were statistically equivalent to each other in terms of mechanical performance, providing the "best" results. These two pieces provided the tightest and most snug fit of the tab within the tab opening. Subjectively, however, it was found that Rev-2C pieces were easier to apply to the fixation tab in that a reasonable amount of force was used to comfortably seat the Rev-2C pieces onto the fixation tabs. Rev-2D pieces were routinely more difficult to apply to the fixation tabs and required an undesirable amount of force to adequately seat the overlying attachment piece on the fixation tab. For this reason, the Rev 2C attachment pieces were deemed "best" because of their outstanding mechanical performance, gains over tabs without attachment pieces, and the ease of use in applying the overlying attachment pieces to the tabs, which would be beneficial in a manufacturing environment. Therefore, the most desirable attachment piece should be capable of receiving a fixation tab with ease and without undue force, but still provide a suitably tight and snug fit of the fixation tab once inserted. The tapered configuration of the tab opening in the pieces provided increased holding and friction fit as the tabs were inserted into the pieces.

It was found that by keeping external dimensions of the overlying attachment piece constant, but gradually tightening the internal opening (slot) dimensions of the piece to create a tighter friction fit around the original end effector (such as a fixation tab), the mechanical performance of the composite end effector was improved. That is, the composite end effector demonstrated higher strength as compared to the unmodified fixation tab.

What is claimed is:

1. A suture device comprising:
   a. an elongated suture body having a proximal end and a distal end; and
   b. a composite end effector at said distal end, said composite end effector comprising:
      i. a fixation tab having a length, width and thickness, and
      ii. an overlying attachment piece, comprising a tab opening with a length, width and thickness,
   wherein the overlying attachment piece further comprising a distal end and a pair of longitudinal slits terminating at the distal end of the overlying attachment piece,
   wherein at least a proximal end of the fixation tab is inserted into said opening of said overlying attachment piece such that the proximal end of the fixation tab abuts a proximal wall of said overlying attachment piece while at least a distal end of the fixation tab extends axially outwardly from the overlying attachment piece and the fixation tab extends laterally outwardly from the overlying attachment piece through the pair of longitudinal slits.

2. The suture device of claim 1, wherein said fixation tab is integrally formed with the distal end of the elongated suture body such that the fixation tab and the elongated suture body are formed from the same material and have a unitary construction.

3. The suture device of claim 1, wherein said overlying attachment piece has a distal end and a proximal end, with a suture opening at the proximal end and the tab opening at the proximal end.

4. The suture device of claim 3, wherein the suture opening has a smaller width than the tab opening.

5. The suture device of claim 1, wherein said suture body comprises a plurality of retainers along at least a portion of its axial length.

6. The suture device of claim 5, wherein said retainers are formed from stamping said suture and retainers from a preform ribbon.

7. The suture device of claim 1, wherein said overlying attachment piece and said fixation tab are joined to each other via friction fit.

8. The suture device of claim 7, wherein said overlying attachment piece and said fixation tab are joined to each other without welding said attachment piece and fixation tab to each other.

9. The suture device of claim 1, wherein said overlying attachment piece and said fixation tab are made from same materials.

10. The suture device of claim 1, wherein said overlying attachment piece and said fixation tab are made from different materials.

11. The suture device of claim 1, wherein the width of the tab opening is tapered such that the distal end of the tab opening has a larger width than the width of the tab opening at said proximal wall.

12. The suture device of claim 1, wherein the thickness of the tab opening is tapered such that the distal end of the tab opening has a larger thickness than the thickness of the tab opening at said proximal wall.

13. A suture device comprising:
   a. an elongated suture body having a proximal end and a distal end, wherein the elongated suture body includes a fixation tab at the distal end such that the elongated suture body terminates at the fixation tab; and
   b. an overlying attachment piece comprising an opening sized to receive the elongated suture body, wherein the opening is configured to receive the fixation tab therein such that at least a portion of the distal end of the elongated suture body is disposed within the overlying attachment piece; the overlying attachment piece further comprising a distal end and a pair of longitudinal slits terminating at the distal end of the overlying attachment piece, such that when the fixation tab is received within the overlying attachment piece the distal end of the fixation tab extends distally from the overlying attachment piece and the fixation tab extends laterally through the pair of longitudinal slits.

14. The suture device of claim 13, wherein the pair of longitudinal slits are in communication with the opening and are sized to receive an outer edge of the fixation tab.

15. The suture device of claim 13, wherein the overlying attachment piece includes a pair of vertical walls disposed within the opening.

16. The suture device of claim 15, wherein the pair of vertical walls are configured to abut the fixation tab such that the pair of vertical walls inhibit the fixation tab from extending through the overlying attachment piece.

* * * * *